United States Patent
Rinaldi et al.

(10) Patent No.: US 12,419,860 B2
(45) Date of Patent: Sep. 23, 2025

(54) TIME RELEASE SLEEP AID SYSTEM

(71) Applicant: NightWise, LLC, Atlanta, GA (US)

(72) Inventors: Danny Rinaldi, Norcross, GA (US); Scott Forsberg, Morgan, UT (US)

(73) Assignee: NightWise, LLC, Atlanta, GA (US)

( * ) Notice: Subject to any disclaimer, the term of this patent is extended or adjusted under 35 U.S.C. 154(b) by 0 days.

(21) Appl. No.: 18/432,512

(22) Filed: Feb. 5, 2024

(65) Prior Publication Data

US 2024/0415810 A1  Dec. 19, 2024

Related U.S. Application Data

(63) Continuation of application No. 17/745,180, filed on May 16, 2022, now Pat. No. 11,890,271, which is a continuation of application No. 16/626,668, filed as application No. PCT/US2018/039746 on Jun. 27, 2018, now Pat. No. 11,351,150.

(60) Provisional application No. 62/525,385, filed on Jun. 27, 2017.

(51) Int. Cl.
| | |
|---|---|
| *A61K 36/00* | (2006.01) |
| *A61K 9/00* | (2006.01) |
| *A61K 31/197* | (2006.01) |
| *A61K 31/4045* | (2006.01) |
| *A61K 31/405* | (2006.01) |
| *A61K 31/519* | (2006.01) |
| *A61K 31/675* | (2006.01) |
| *A61K 31/714* | (2006.01) |
| *A61K 33/06* | (2006.01) |
| *A61K 36/185* | (2006.01) |
| *A61K 36/53* | (2006.01) |
| *A61K 36/756* | (2006.01) |
| *A61K 36/84* | (2006.01) |

(52) U.S. Cl.
CPC ........ *A61K 31/4045* (2013.01); *A61K 9/0056* (2013.01); *A61K 31/197* (2013.01); *A61K 31/405* (2013.01); *A61K 31/519* (2013.01); *A61K 31/675* (2013.01); *A61K 31/714* (2013.01); *A61K 33/06* (2013.01); *A61K 36/185* (2013.01); *A61K 36/53* (2013.01); *A61K 36/756* (2013.01); *A61K 36/84* (2013.01)

(58) Field of Classification Search
CPC ...................................................... A61P 25/02
See application file for complete search history.

(56) References Cited

U.S. PATENT DOCUMENTS

| | | |
|---|---|---|
| 8,545,892 B2 | 10/2013 | Niichel |
| 2001/0011083 A1 | 8/2001 | Barr et al. |
| 2005/0031688 A1 | 2/2005 | Ayala |
| 2005/0069580 A1 | 3/2005 | Hirsh et al. |
| 2008/0009505 A1 | 1/2008 | Hodges et al. |
| 2008/0171085 A1 | 7/2008 | Elnekave et al. |
| 2008/0254121 A1* | 10/2008 | Clement ............... A23L 33/105 514/415 |
| 2012/0294952 A1 | 11/2012 | Zarbock et al. |
| 2013/0064804 A1 | 3/2013 | Naidu et al. |
| 2014/0271890 A1 | 9/2014 | Ahmad |
| 2015/0071993 A1 | 3/2015 | Patel et al. |
| 2016/0243038 A1 | 8/2016 | Shah et al. |

FOREIGN PATENT DOCUMENTS

| | | | |
|---|---|---|---|
| CN | 101132777 A | 2/2008 | |
| CN | 101156855 A * | 4/2008 | ........... A61K 31/519 |
| CN | 103550775 A | 2/2014 | |
| JP | 2009527504 A | 7/2009 | |
| RU | 2013119044 A | 10/2014 | |
| WO | 2005044199 A1 | 5/2005 | |

OTHER PUBLICATIONS

Anonymous: "Sleep Formula 39," Sep. 13, 2016 (Sep. 13, 2016), XP055769020, Retrieved from the Internet: URL: https://web.archive.org/web/20160913172954/http://www.harmonixsleep.com/sleep-formula-39.html.

Database GNPD [Online] Mintel; Jul. 23, 2007 (Jul. 23, 2007), anonymous: "Liquid Sleeping Aid Drops", XP055600005, Database accession No. 743321.

Database GNPD [Online] Mintel; Sep. 21, 2012 (Sep. 21, 2012), anonymous: Sleep Formula 39, XP055768760, Database accession No. 1890600.

English translation of Office Action for Chinese Application No. 201880053631.6 dated Nov. 10, 2022.

English translation of Office Action for Indian Application No. 202017002067 dated Jul. 11, 2023.

English translation of Office Action for Japanese Application No. 2020-522282 dated Apr. 18, 2023.

(Continued)

*Primary Examiner* — Qiuwen Mi

(74) *Attorney, Agent, or Firm* — Meunier Carlin & Curfman LLC

(57) ABSTRACT

Compositions for treating a sleep disorder or modifying or improving the sleep-wake cycle in a subject are disclosed herein. In some examples, the composition can comprise one or more sleep promoting active agents, one or more sleep quality active agents, one or more sleep recovery active agents, and optionally one or more next day active agents. The composition can provide an immediate burst release of the one or more sleep promoting active agents, a delayed burst or delayed sustained release of the one or more sleep quality active agents, a delayed burst or delayed sustained release of the one or more sleep recovery active agents, and a delayed burst or delayed sustained release of the one or more next day active agents. The composition can be provided as a daily oral uni-dosage form Methods of making and using the compositions are also provided.

10 Claims, 2 Drawing Sheets

(56) References Cited

OTHER PUBLICATIONS

Head Kathleen A et al: "Nutrients and botanicals for treatment of stress: adrenal fatigue, neurotransmitter imbalance, anxiety, and restless sleep," Alternative Medicine Review, Thorne Research Inc., Sandpoint, US, vol. 14, No. 2, Jun. 1, 2009 (Jun. 1, 2009), pp. 114-140.
International Preliminary Report on Patentability issued for Application No. PCT/US2018/039746, dated Jan. 9, 2020.
International Search Report and Written Opinion issued in corresponding PCT Application No. PCT/US2018/039746, dated Nov. 5, 2018, 13 pages.
Office Action for Australian Application No. 2018292531 dated Jul. 19, 2023.
Office Action issued for Japanese Application No. 2020-522282, dated Jul. 26, 2022.
Rosekind, Mark R. "The epidemiology and occurrence of insomnia." The Journal of clinical psychiatry 53 (1992): 4-6. Abstract.
Supplementary European Search Report issued in corresponding application No. EP 18825110, dated Feb. 8, 2021, 11 pages.
Treisman et al., "Insomnia," Johns Hopkins POC-IT Center, 2010 pp. 1-3.
English translation of Search Report for Chinese Application No. 201880053631.6 dated Nov. 2, 2022.
"Liquid Sleeping Aid Drops", GNPD, Mintel, URL: https://www.gnpd.com/sinatra/recordpage/743321/, XP055600005.
"Sleep Formula 39", GNPD, Mintel, URL: https://www.gnpd.com/sinatra/recordpage/1890600/, XP055768760.

* cited by examiner

TIME RELEASE SLEEP AID SYSTEM

FIELD

This disclosure relates generally to sleep aids, more particularly to time release sleep aids.

BACKGROUND

Sleep disorders such as insomnia or alterations in the sleep-wake cycle are common in human beings. It has been shown in a Gallup poll survey that 95% of the adult population had experienced insomnia (Rosekind, M., *J Clin. Psychiatry*, 1992, 53:4-6). The current literature maintains consistently that approximately one third of all people have sleep problems in any given year.

Sleep disorders can have serious consequences by themselves and can lead to numerous other medical problems. As a result, numerous remedies and methods have been created to deal with sleep disorders. See Treisman et al., "Insomnia," Johns Hopkins POC-IT Center, 2010 pp. 1-3. Some examples of sleep medications include over-the-counter medicines such as TYLENOL PM™, compositions containing melatonin, herbal remedies, as well as pharmaceuticals such as zolpidem, quetiapine, and many others. While some of these sleep medications may be effective, tolerance generally develops for most medications requiring increasingly higher dosages. Other sleep medications either do not work well, have serious side effects, or both. For example, some medications do not continue to work over extended periods and the patient wakes up during the night.

There is a significant need for a sleep composition and method that is safe and effective. There is also a need for a sleep composition that is effective over an extended period, and does not have significant side effects. The compositions and methods disclosed herein address these and other needs.

SUMMARY

Compositions that provide a modified release profile of active agents are disclosed herein. Active agent is used interchangeably with the terms "ingredient," "active ingredient," "compound," "active compound" or "substance." The active agents can include one or more sleep promoting active agents, one or more sleep quality active agents, and/or one or more sleep recovery active agents, and optionally one or more next day active agent. For example, in some aspects, the compositions can comprise one or more sleep promoting active agents, one or more sleep quality active agents, one or more sleep recovery active agents, and optionally one or more next day active agent. In some aspects, the compositions can comprise one or more sleep promoting active agents, one or more sleep quality active agents, and optionally one or more next day active agents. In some aspects, the compositions can comprise one or more sleep promoting active agents, optionally one or more sleep recovery active agents, and one or more next day active agents. In some aspects, the composition can comprise one or more sleep quality active agents, one or more sleep recovery active agents, and optionally one or more next day active agents. In some aspects, the composition can comprise one or more sleep quality active agents and one or more next day active agents. In some aspects, the composition can comprise one or more sleep recovery active agents and one or more next day active agents.

When administered, the disclosed compositions can provide an immediate burst release or immediate sustained release of the sleep promoting active agent, a delayed burst release or delayed sustained release of the sleep quality active agent, a delayed burst release or delayed sustained release of the sleep recovery active agent, and/or delayed burst release or delayed sustained release the next day active agent. In some aspects, the composition can provide an immediate burst release of the sleep promoting active agent within about 30 minutes, preferably within about 15 minutes of administration. The composition can also provide delayed sustained and/or delayed burst release of the sleep quality active agent within about 6 hours, such as within about 4.5 hours, from about 1 to about 6 hours, preferably from about 2 to about 5 hours, more preferably from about 2.5 to about 4.5 hours of administration. The composition can further provide delayed burst and/or delayed sustained release of the sleep recovery active agent and/or the next day active agent after about 3 hours, such as after about 4, after about 5, or after about 6 hours, preferably after about 6 to about 8.5 hours, more preferably after about 6.5 to about 8.5 hours of administration. Methods of making and using the compositions are also provided herein.

The active agents of the disclosed compositions can include a phytochemical, an herbal extract, a vitamin, a hormone, an amino acid, or mineral. For example, the sleep promoting active agent and/or the sleep quality active agent can be independently selected from the group consisting of y-aminobutyric acid (GABA), glycine, hydroxytryptophan, riboflavin, melatonin, nicotinamide, picamilon, L-taurine, L-theanine, 4-amino-3-phenylbutyric acid, L-tryptophan, calcium, calcium D-glucarate, calcium gluconate, calcium lactate, zinc, iron, magnesium, magnesium glycinate, magnesium taurate, magnesium chloride, magnesium citrate, magnesium oxide, magnesium amino acid chelate, isoflavone, astaxanthin, phosphatidylserine, glutamine, phenibut 4-amino-3-phenylbutyric acid o, a milk peptide, a milk protein hydrolysate, lactium, plant extracts, blends thereof, and combinations thereof. In specific examples, the composition can include at least two sleep promoting active agents selected from the group consisting of melatonin, lactium, L-tryptophan, y-aminobutyric acid, and magnesium. In other specific examples, the composition can include at least two sleep quality active agents selected from the group consisting of an extract from *Valeriana officinalis* (root), an extract from *Melissa officinalis*, an extract from *Phellodendron amurense*, and an extract from *Humulus lupus*.

The sleep recovery active agent and/or the next day active agent can be independently selected from L-theanine, L-taurine, y-aminobutyric acid, glycine, folic acid, (6S)-5-methyltetrahydrofolic acid or a salt thereof, inositol, riboflavin 5'-phosphate or a salt thereof, vitamin A, vitamin B12, methylcobalamin, cyanocobalamin, vitamin B3, vitamin B5, vitamin B6, pyridoxal 5'-phosphate, pyridoxine, vitamin B9, vitamin C, vitamin D3, a xanthine, camosin, alpha-glycerylphosphoryl choline, lecithin, cytidine diphosphate choline, phosphatidylserine, ATP, ribose, magnesium, coenzyme Q10, plant extracts, or combinations thereof. In specific examples, the composition can include at least two sleep recovery active agents selected from the group consisting of an extract from cocao, L-theanine, vitamin B5, vitamin B6, vitamin B12, and folic acid, preferably at least one of vitamin B5, vitamin B6, or vitamin B12 and at least one of an extract from cocao, L-theanine, or folic acid.

The disclosed compositions can be prepared as, for example, a single bead (such as single-layered or multilayered particles) comprising the active agents. For example, the composition can be a multilayered particle comprising any two or more of the sleep promoting active agents, the sleep quality active agents, the sleep recovery active agent, and/or the next day active agent. Each layer of the multi-layered particle optionally includes a binder as described herein. In other examples, the composition can be a single-layered particle comprising the sleep promoting active agent and an optional binder. The optional binder can include a taste masking agent. In further examples, the composition can be a single-layered particle comprising the sleep quality active agent and a polymeric binder. In still further examples, the composition can be a single-layered particle comprising the sleep recovery active agent and a polymeric binder. In further examples, the composition can be a single-layered particle comprising the next day active agent and a polymeric binder. Suitable polymeric binders can include methyl cellulose, ethyl cellulose, microcrystalline cellulose, croscarmellose sodium, dicalcium phosphate, cellulose, hypromellose, hydroxypropyl methylcellulose, carboxymethylcellulose, alkali metal carboxymethyl cellulose, carboxyethyl cellulose, hydroxymethyl cellulose, hydroxyethyl cellulose, hydroxypropyl cellulose, and combinations thereof. Additional coating layers, a thicker coating layer, and/or a crosslinked coating layer on the bead can result in a delayed and/or slower release of the active agent.

The disclosed compositions can be prepared as a combination of separate beads and/or powders. In some examples, the sleep quality active agent can be prepared as a single bead comprising one or more sleep quality active agents encapsulated by a polymeric binder. In some examples, the sleep recovery active agent and/or the next day active agent can be prepared as a single bead comprising one or more sleep recovery active agents and/or the next day active agent encapsulated by a polymeric binder. In some examples, the sleep promoting active agent can be coated onto the surface of one or more of the beads. Alternatively, the sleep promoting active agents can be a free powder used in combination with the bead comprising the sleep quality active agent and the bead comprising the sleep recovery active agent, and the next day active agent.

The sleep quality active agent can be in an amount of from about 0.5 wt % to about 55 wt %, based on the combined weight of the sleep quality active agent and the polymeric binder. The sleep recovery active agent can be in an amount of from about 0.5 wt % to about 55 wt %, based on the combined weight of the sleep recovery active agent and the polymeric binder. The next day active agent can be in an amount of from about 0.5 wt % to about 55 wt %, based on the combined weight of the next day active agent and the polymeric binder.

The composition can be dispersed in a comestible matrix as a daily oral dosage form. The comestible matrix can be a solid, a semi-solid, a solution, a suspension, or an emulsion. In some examples, the comestible matrix can be selected from the group consisting of chocolate, chewing gum, lozenge, soft candy, snack bar, capsule, soft chew, gummies, powder, tablet, or a drinkable preparation.

Methods of using the compositions are also provided herein. In some examples, the method can include administering any one of the composition described herein as a daily oral single dosage form.

Methods of treating a sleep disorder for example, modifying or improving the sleep-wake cycle in a subject comprising administering a sleep promoting active agent that when administered provides an immediate burst release of the sleep promoting active agent within about 30 minutes of administration (such as within about 10 minutes or within about 20 minutes of administration), administering a sleep quality active agent in the form of a delayed burst or delayed sustained release to supply the sleep quality active agent within about 6 hours of administration (such as within about 1 hour, within about 2 hours, within about 3 hours, within about 4 hours, within about 5 hours, or from about 2.5 to about 4.5 hours of administration), administering a sleep recovery active agent after about 3 hours (such as after about 4, after about 5, after about 6 hours or from about 6.5 to about 8.5 hours of administration of the sleep promoting active agent), and/or administering a next day active agent after about 3 hours (such as after about 4, after about 5, or after about 6 hours of administration of the sleep promoting active agent), are also described.

BRIEF DESCRIPTION OF THE FIGURES

The accompanying figures, which are incorporated in and constitute a part of this specification, illustrate several aspects described below.

FIG. 2A is a control, which shows the sleep pattern of an untreated subject. FIG. 2B shows the sleep pattern of a subject after administration of a burst-release bead comprising an active agent.

DETAILED DESCRIPTION

Figure 1:
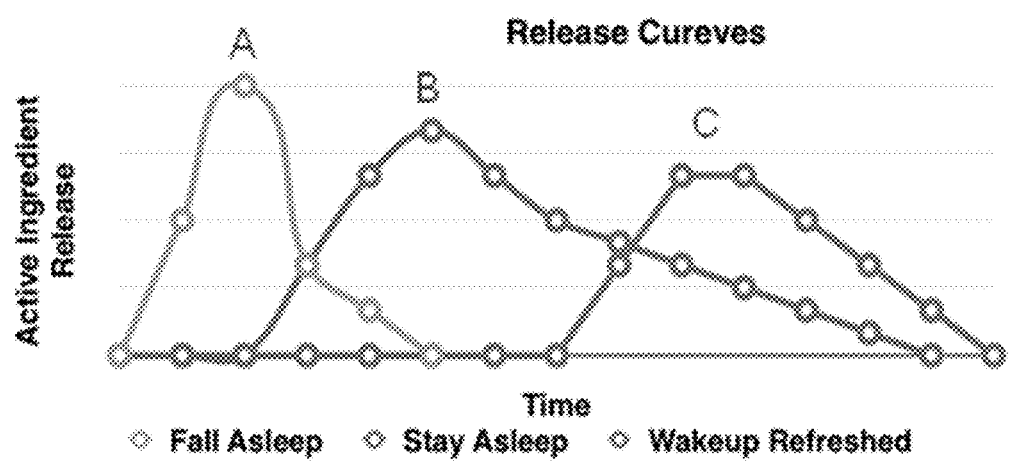
FIG. 1 is a graph showing the release curves of the active ingredients in a sustained-release bead.

Compositions that provide a modified release profile of active agents are disclosed herein. The active agents can include one or more sleep promoting active agents, one or more sleep quality active agents, and/or one or more sleep recovery active agents, and optionally one or more next day active agent. The one or more sleep quality active agents, one or more sleep recovery active agents, and/or one or more next day active agents can be combined with a binder, which can include a polymeric binding agent.

"Modified release" as used herein refers to a change in the availability or release profile of an active agent or a portion thereof from its dosage form compared to the availability or release profile of the active agent in its conventional unmodified form. "Modified release" can be evidenced by modified dissolution characteristics of the active agent in its dosage form compared to the active agent alone. Modified release can encompass sustained release, controlled release, timed release, burst release, prolonged release, delayed release, immediate release, slow release, extended release, or combinations thereof. As is also known in the art, suitable mechanisms for achieving modified release of an active agent include diffusion, erosion, surface area control via geometry and/or impermeable barriers, semi-permeable barriers and other known mechanisms known. In some examples, the disclosed composition can provide an immediate burst release, delayed burst release, and/or delayed sustained release of the active agents in the composition. Methods of making and using the compositions disclosed herein are also provided.

Before the present compositions and/or methods are described, it is to be understood that this disclosure is not limited to specific active agents, such as specific sleep promoting active agents or particular sleep recovery active agents, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a polymeric binder" includes mixtures of polymeric binders, reference to "an active agent" includes mixtures of active agents, reference to "the sleep promoting active agent" includes mixtures of two or more such sleep promoting active agents, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

By "treat" or other forms of the word, such as "treated", "treating", or "treatment," is meant to administer a composition or to perform a method in order to reduce or prevent a particular characteristic or event (e.g., sleep disorder). The term "control" is used synonymously with the term "treat." To treat a sleep disorder, according to the methods described herein, the treatment does not necessarily provide therapy for the underlying pathology that is causing the sleep disorder sensation. Treatment of a sleep disorder can be purely symptomatic. For example, treatment of a sleep disorder can include modifying or improving the sleep-wake cycle of a subject.

The term "active agent" is used interchangeably with the terms "ingredient," "active ingredient," "substance," or "compound," and refers to a pharmacological agent that can act locally or systemically in the body. The term "active agent" includes agents that can be administered to a subject for the treatment or prevention of a disorder.

It is understood that throughout this specification the identifiers "first" and "second" are used solely to aid in distinguishing the various active agents, features, and steps of the disclosed subject matter. The identifiers "first" and "second" are not intended to imply any particular order, amount, preference, or importance to the active agents or steps modified by these terms.

Reference will now be made in detail to specific aspects of the disclosed materials, active agents, compositions, articles, and methods, examples of which are illustrated in the accompanying Examples.

Active Agents

The compositions described herein can include one or more sleep promoting active agents. "Sleep promoting active agent" as used herein refers to an active agent that induces calming of mental excitement or abates physiological function. Sleep promoting active agents can include all active agents having a sleep promoting active agent action. For example, sleep promoting active agents can include a skeletal muscle relaxant, an anti-anxiety active agent, an active agent that reduces stress, high blood pressure, or hypertension, an active agent that promote relaxation, an active agent that decreases sleep onset latency, or combinations thereof. In some aspects, the sleep promoting active agent can be naturally occurring. For example, the sleep promoting active agent can be selected from the group consisting of a phytochemical, an herbal extract, a vitamin, a hormone, an amino acid, a mineral, or a combination thereof. Preferably, the sleep promoting active agent is non-addictive.

The compositions described herein can also include one or more sleep quality active agents. "Sleep quality active agent" as used herein refers to an active agent that helps to stay asleep, for example, it helps to sustain REM sleep and/or decrease wakefulness during sleep. Sleep quality active agent can include all active agents having a sleep quality active agent action. For example, sleep quality active agents can include an active agent that increases sleep re-initiation, increase sleep maintenance, increase sleep duration, decrease sleep disturbance, or combinations thereof. The sleep quality active agent can be naturally occurring. For example, the sleep quality active agent can be selected from the group consisting of a phytochemical, an herbal extract, a vitamin, a hormone, an amino acid, a mineral, or a combination thereof. Preferably, the sleep quality active agent is non-addictive. In some aspects, the sleep promoting active agent and the sleep quality active agent are different. In some aspects, the sleep promoting active agent and the sleep quality active agent are the same.

The compositions described herein can include one or more (such as two or more, three or more, four or more, or five or more) sleep promoting active agents and/or one or more (such as two or more, three or more, four or more, or five or more) sleep quality active agents. Examples of suitable sleep promoting active agents and/or sleep quality active agents can include, but are not limited to, γ-aminobutyric acid (GABA), glycine, hydroxytryptophan or a derivative thereof, picamilon or a derivative thereof, L-taurine or a derivative thereof, nicotinamide or a derivative thereof, L-theanine or a derivative thereof, 4-amino-3-phenylbutyric acid or a derivative thereof, L-tryptophan or a derivative thereof, calcium, calcium D-glucarate or a derivative thereof, calcium gluconate or a derivative thereof, calcium lactate or a derivative thereof, zinc, iron, magnesium, magnesium glycinate or a derivative thereof, magnesium taurate or a derivative thereof, magnesium chloride, magnesium citrate, magnesium oxide, magnesium amino acid chelate, isoflavone or a derivative thereof, astaxanthin or a derivative thereof, phosphatidylserine or a derivative thereof, glutamine or a derivative thereof, phenibut 4-amino-3-phenylbutyric acid or a derivative thereof, a milk peptide or a derivative thereof, a milk protein hydrolysate or a derivative thereof, lactium, Kava, Skullcap, lemon balm extract, passion flower extract, hops extract, chamomile extract, ashwagandha extract, jujube extract, catnip extract, Ashwagandha extract, picamilon extract, extract from *Magnolia officinalis* (bark), extract from Holy Basil, Tulsi, extract from *Humulus lupulus*, extract from *Phellodendron amurense* (bark), extract from *Valeriana officinalis* (root), extract from *Hemerocallis Julva* var. *sempervirens*, extract from *Albizzia julibrissin Durazz*, eicosapentaenoic acid (EPA), extract from St. John's wort, extract from *Bacopa monnieri*, Chinese herbal medicines, extract from *Apocynum venetum* (luobuma), extract from *Ganoderma lucidum* (reishi), extract from *Matricaria chamomilla*, extract from *Albizia julibrissin*, extract from *Melissa officinalis* (leaf), extract from *Hemerocallis Julva* var. *sempervirens*, phosphatidyl serine, blends thereof, or combinations thereof. Extracts from *Magnolia officinalis* and *Phellodendron amurense* are commercially available, for example, under the trade name RELORA™.

The compositions described herein can also include one or more sleep recovery active agents. "Sleep recovery" as used herein refers to an increase feeling of being rested on waking, increase alertness, increase energy, increase mood, increase focus, and/or enhanced mental acuity or cognitive performance. Sleep recovery can be determined by the manner or quality of action taken to carry out a task on waking, for example, enhanced mental acuity refers to the improved ability to carry out that task or multiple sequential tasks. Sleep recovery may include improved comprehension and improved memory retention. The sleep recovery active agent can be naturally occurring. For example, the sleep recovery active agent can be selected from the group consisting of a phytochemical, an herbal extract, a vitamin, a hormone, an amino acid, a mineral, or a combination thereof. Preferably, the sleep recovery active agent is non-addictive.

Examples of suitable sleep recovery active agents include, but are not limited to, L-theanine or derivatives thereof, L-taurine or derivatives thereof, y-aminobutyric acid or derivatives thereof, glycine or derivatives thereof, folic acid or derivatives thereof, (6S)-5-methyltetrahydrofolic acid or a salt or derivatives thereof, inositol or derivatives thereof, riboflavin 5'-phosphate or a salt or derivatives thereof, vitamin A or derivatives thereof, vitamin B12 or derivatives thereof, methylcobalamin or derivatives thereof, cyanocobalamin or derivatives thereof, vitamin B3 or derivatives thereof, vitamin B5 or derivatives thereof, vitamin B6 or derivatives thereof, pyridoxal 5'-phosphate or derivatives thereof, pyridoxine or derivatives thereof, vitamin B9 or derivatives thereof, vitamin C or derivatives thereof, vitamin D3 or derivatives thereof, a xanthine or derivatives thereof, camosin or derivatives thereof, alpha-glycerylphosphoryl choline or derivatives thereof, lecithin or derivatives thereof, cytidine diphosphate choline or derivatives thereof, acetyl choline, phosphatidyl serine or derivatives thereof, ATP, ribose, magnesium, coenzyme Q10, extract from *Coleus forskohlii*, extract from *Bacopa monnieri*, caffeine, ephedra, vincamine, chocamine, extract from cocoa extract, extract from *Ginkgo biloba* (leaf), *Panax ginseng*, extract from *Eleutherococcus senticosus*, extract from *Centella asiatica*, peppermint extract, rosemary extract, wild oats extract, blends thereof, or combinations thereof. U.S. Patent Application Publication No. 2008/0009505 describes theanine derivatives, the disclosure of which is incorporated herein by reference. Theanine can be obtained commercially under the trade name SUNTHEANINE™.

The compositions described herein can also include one or more next day active agents. "Next day" active agent as used herein refers to an active agent that promotes the maintenance of normal circadian rhythms and/or provide a nutrient for the production of endogenous sleep promoting active agents. Suitable examples of next day ingredients include, but are not limited to folic acid or derivatives thereof, (6S)-5-methyltetrahydrofolic acid or salts or derivatives thereof, inositol or derivatives thereof, riboflavin 5'-phosphate or salts or derivatives thereof, vitamin A or derivatives thereof, vitamin B12 or derivatives thereof, cyanocobalamin or derivatives thereof, methylcobalamin or derivatives thereof, vitamin B3 or derivatives thereof, vitamin B5 or derivatives thereof, vitamin B6 or derivatives thereof, pyridoxine or derivatives thereof, vitamin B9 or derivatives thereof, vitamin C or derivatives thereof, vitamin D3 or derivatives thereof, alpha-glycerylphosphoryl choline or derivatives thereof, lecithin or derivatives thereof, cytidine diphosphate-choline or derivatives thereof, acetyl choline, phosphatidyl serine or derivatives thereof, ATP, *Coleus Forskohlii* extract, glycine, ribose, magnesium, coenzyme Q1O, and combinations thereof.

In some examples, the disclosed compositions can comprise one or more sleep promoting active agents, one or more sleep quality active agents, one or more sleep recovery active agents, and optionally one or more next day active agents. In other examples, the composition can comprise one or more sleep promoting active agents, one or more sleep quality active agents, and optionally one or more next day active agents. In still other examples, the composition can comprise one or more sleep promoting active agents, optionally one or more sleep recovery active agents, and one or more next day active agents. In further examples, the composition can comprise one or more sleep quality active agents, one or more sleep recovery active agents, and optionally one or more next day active agents. In even further examples, the composition can comprise one or more sleep quality active agents and one or more next day active agents. In some examples, the composition can comprise one or more sleep recovery active agents and one or more next day active agents.

The amount of the active agents in the composition is not limited. In some examples, the active agents can be present in an amount of from about 0.1 wt % to about 90 wt % of the composition. For example, the amount of active agents can be from about 0.1 wt % to about 60 wt %, about 0.5 wt % to about 50 wt %, or about 1 wt % to about 50 wt % of the composition.

Representative ranges for the active ingredients in the compositions disclosed herein are provided in Table 1. In some embodiments, the compositions can include two or more of each "sleep promoting," "sleep quality," and "sleep recovery" active agents listed in Table 1.

TABLE 1

| Sleep Formulation. | | | |
|---|---|---|---|
| Sleep Promoting (Sleep Onset Latency) Active Agents for Immediate Release | | | |
| Melatonin/mg | 0.01-10 | 0.05-5 | 0.1-1 |
| Lactium (milk peptides)/mg | 25-500 | 50-200 | 75-150 |
| L-tryptophan/mg | 50-1000 | 100-500 | 150-250 |
| GABA (gamma-aminobutyric acid)/mg | 25-500 | 25-250 | 50-150 |
| Magnesium (from magnesium oxide)/mg | 50-1000 | 100-500 | 200-300 |
| Sleep Quality (Sleep Maintenance) Active Agents for Release from about 2.5 to 4.5 hours | | | |
| Valerian root extract/mg | 25-1000 | 25-500 | 100-200 |
| Relora (*Magnolia officinalis* and *Phellodendron amurense* extracts)/mg | 25-1000 | 25-500 | 100-200 |
| Lemon Balm (*Melissa officinalis*) extract/mg | 10-250 | 10-150 | 30-50 |
| Hops extract (*Humulus lupus*) I mg | 10-250 | 10-150 | 20-40 |
| Sleep Recovery and/or Next Day (Morning Recovery) Active Agents for Release 6.5 to 8.5 hours | | | |
| Cocoa Extract I mg | 50-1000 | 100-500 | 280-320 |
| L-Theanine/mg | 10-250 | 10-150 | 35-60 |
| Vitamin B5 (7.8% calcium 87% pantothenate)/mg | 10-250 | 10-150 | 30-50 |
| Vitamin B6 (pyridoxine HCL, USP)/mg | 0.01-10 | 0.05-6 | 1-3 |
| Vitamin B12 (cyanocobalamin 1% trituration)/mg | 0.01-5 | 0.05-1 | 0.25-0.5 |
| Folic Acid (97 to 102 using USB)/mg | 0.01-5 | 0.05-1 | 0.3-0.5 |

Binder

The compositions described herein can include a binder. The binder can be biocompatible. "Biocompatible" or "biologically compatible", as used herein, generally refer to binding agents that are, along with any metabolites or degradation products thereof, generally non-toxic to cells and tissues, and which do not cause any significant adverse effects to cells and tissues when cells and tissues are incubated (e.g., cultured) in their presence. In some examples, the biocompatible binding agent can be generally recognized as safe (GRAS) compliant. GRAS status is an American Food and Drug Administration (FDA) designation that a chemical or active agent added to food is considered safe by experts, and so is exempted from the usual Federal Food, Drug, and Cosmetic Act (FFDCA) food additive tolerance requirements.

In some aspects of the present disclosure, the binder can be a polymeric binding agent. Examples of suitable polymeric binding agents include, but are not limited to, methyl cellulose, ethyl cellulose, microcrystalline cellulose, croscarmellose sodium, dicalcium phosphate, cellulose, hypromellose, hydroxypropyl methylcellulose, carboxymethylcellulose, alkali metal carboxymethyl cellulose, carboxyethyl cellulose, hydroxymethyl cellulose, hydroxyethyl cellulose, hydroxypropyl cellulose, or combinations thereof. Other exemplary binders can include xanthan gum, viscarin, gelatin, starch, glucose, sucrose, polyvinyl pyrollidone, polyvinyl alcohol, gum tragacanth, gum karaya, sodium alginate, Laponite CP or SP, or magnesium aluminum silicate gel. The binder can also be coloring agents, taste masking agents, or combinations thereof. In some examples, cellulose-based binders are used.

Any suitable amount of the binder can be used in the compositions herein. For example, the amount of binder can be from about 0.5 wt % to about 99.9 wt % of the composition. For example, the amount of binder can be from about 1 wt % to about 99 wt %, from about 1 wt % to about 98 wt %, from about 1 wt % to about 95 wt %, from about 5 wt % to about 95 wt %, from about 10 wt % to about 95 wt %, from about 20 wt % to about 95 wt %, from about 30 wt % to about 95 wt %, about 40 wt % to about 95 wt %, or about 30 wt % to about 90 wt % of the composition. The amount and/or type of binder included in the composition may be adjusted in order to alter the release profile of the active agents. For example, the amount and/or type of polymeric binding agent encapsulating the active agent may be adjusted to exhibit a sustained release or delayed release profile of the active agent. "Encapsulation" as used herein, refers to an agent, for example an active agent, residing primarily within a binder system as opposed to merely residing upon or attaching to the surface of the binder system In some embodiments, encapsulation of the active agent refers to the active agent dispersed or encased within the binder.

Comestible Matrix

The composition comprising the active agents and the binder can be dispersed in a comestible matrix. The comestible matrix can be a solid, a semi-solid, or a liquid. For example, the comestible matrix can be a powder, a solution, a suspension, or an emulsion. The comestible matrix can be in a form suitable for oral administration, such as a tablet, a capsule, a powder, a granule, or a drinkable preparation. For example, the comestible matrix can include chocolate, marshmallow, hard candy, soft candy, soft chew, taffy, sugarless candies, desserts such as jelly and pudding, confectionery such as cakes, cookies, chewing gum, bubble gum, granola bars, gel beads, gelatin candies, pectin candies, gummies, powdered confectionary for example a stick pack powder, starch candies, lozenges, frozen confectionery such as ice creams, sherbets, and ice-lolly, a beverage, crackers, biscuits, cookies, cakes, breads, capsules, pills, or tablets. In some examples, the comestible matrix is a chocolate matrix. In some examples, the comestible matrix can also be a chew. In other examples, the comestible matrix is a powder that can be added to a beverage such as flavored water, a shot beverage, a multi-dose beverage, tea, concentrated fruit juice, straight juice, carbonated drink, soft drink, or milk beverage. In further examples, the composition can be in the form of a tablet or capsule that can be administered with a beverage such as water, juice, or a dink. The tablet or capsule can be formulated as a chewable formulation.

Modified Release Compositions

When administered to a subject, the disclosed compositions can release certain active agents at certain periods, rather than all at once. For example, the disclosed compositions can (i) release the sleep promoting active agent immediately or within about 30 minutes of administration (immediate burst release) or over a period of about 3 hours beginning immediately or within 30 minutes of administration (immediate sustained release) (ii) release the sleep quality active agent over a period of about 6 hours of administration (sustained or burst release), and/or (iii) release the sleep recovery active agent and/or the optional next day active agent after about 3 hours or more of administration (delayed burst or delayed sustained).

The sleep promoting active agent for immediate burst release can include a composition comprising the sleep promoting active agent and optionally a binder. In some examples, the optional binder includes a material to alter the appearance, taste, smell, or shelf life of the sleep promoting active agent. The sleep promoting active agent can be encapsulated in the optional binder.

The sleep quality active agent can be in the form of a composition comprising the sleep quality active agent and a polymeric binder. The sleep quality active agent and the polymeric binder can be prepared for sustained release, delayed sustained release, or delayed burst release. The sleep quality active agent can be homogenously mixed or encapsulated within (coated) with the polymeric binder. For example, the sleep quality active agent for sustained release can include a composition comprising the sleep quality active agent and a sustained release polymeric binder homogenously mixed. In some examples, the sleep quality active agent for delayed sustained release can include the sustained release active agent (i.e., the sleep quality active agent and the sustained release polymeric binder) coated with a delayed release polymeric binder. In specific examples, the sustained release polymeric binder and/or the delayed release polymeric binder can include a polymer selected from polyacrylate, methylcellulose, CARBOWAX™, or combinations thereof. In some aspects, the release of the active agent can be controlled through a thicker coating layer, pH, osmotic control, or combinations thereof.

The sleep quality active agent can be in an amount of from about 0.5 wt % to about 55 wt %, based on the combined weight of the sleep quality active agent and the polymeric binder. The polymeric binder can be in an amount of from about 0.5 wt % to about 99.9 wt %, such as from about 50 wt % to about 99.8 wt %, based on the combined weight of the sleep quality active agent and the polymeric binder.

The sleep recovery active agent can be in the form of a composition comprising the sleep recovery active agent and a polymeric binder. The sleep recovery active agent and the polymeric binder can be prepared for sustained release, delayed sustained release, or delayed burst release. The sleep recovery active agent can be homogenously mixed or encapsulated within (coated) with the polymeric binder. For example, the sleep recovery active agent for sustained release can include a composition comprising the sleep recovery active agent and a sustained release polymeric binder homogenously mixed. In some examples, the sleep recovery active agent for delayed sustained release can include the sustained release active agent (i.e., the sleep recovery active agent and the sustained release polymeric binder) coated with a delayed release polymeric binder. In some examples, the sleep recovery active agent for delayed burst release can include the sleep recovery active agent coated with a delayed release polymeric binder. In specific examples, the delayed release polymeric binder can include a polymer selected from polyacrylate, methylcellulose, CARBOWAX™, or combinations thereof. The sleep recovery active agent can be in an amount of from about 0.5 wt % to about 55 wt %, based on the combined weight of the sleep recovery active agent and the polymeric binder. The polymeric binder can be in an amount of from about 0.5 wt % to about 99.9 wt %, such as from about 50 wt % to about 99.8 wt %, based on the combined weight of the sleep recovery active agent and the polymeric binder.

The next day active agent can include a composition comprising the next day active agent and optionally a polymeric binder. The next day active agent and the polymeric binder can be prepared for sustained release, delayed sustained release, or delayed burst release. In some examples, the next day active agent for sustained release can include a composition comprising the next day active agent and a sustained release polymeric binder homogenously mixed. In some examples, the next day active agent for delayed sustained release can include the sustained release active agent (i.e., the next day active agent and the sustained release polymeric binder) coated with a delayed release polymeric binder. In some examples, the next day active agent for delayed burst release can include the next day active agent coated with a delayed release polymeric binder. The next day active agent can be in an amount of from about 0.5 wt % to about 55 wt %, based on the combined weight of the next day active agent and the polymeric binder. The next day active agent can be combined with the sleep recovery active agent, having the same release profile as the sleep recovery active agent.

In some examples, the composition containing the sleep promoting active agent, the sleep quality active agents, the sleep recovery active agent, and optionally the next day active agent can be formulated as a single unit composition. The single unit composition can be any suitable shape such as spherical, substantially spherical, flaked, rod shaped, square, oval, as well as any type of irregular shape. For example, the single unit composition can be rod-shaped bead, wherein the sleep promoting active agent can be located at the terminal ends of the bead, the sleep recovery active agent and optional next day active agent can be located in the middle of the bead, and the sleep quality active agent can be located between the terminal and central portions of the bead. In another example, the single unit composition can be a spherical bead (for example a multilayered particle) comprising the sleep promoting active agent on the surface, the sleep recovery active agent and optional next day active agent at the center, and the sleep quality active agent in between the sleep promoting active agent and sleep recovery active agent or throughout the bead. Thus, when the bead is ingested and digested, the timing of the release of the various active agents is in accordance with the timing of the bead's degradation in the gut or lower intestine. The active agent can be present in each layer for example, as a nanoparticle, a microparticle or a granule (including the active agent and a binder) or in its native form (that is, the active agent alone, not mixed with a binder). In some embodiments, the active agent (in the form of a nanoparticle, a microparticle, a granule, or its native form) can be combined with an additional material (such as a binder or bulking agent) to form a layer of the single unit or multi-unit composition.

In some examples, the sleep quality active agent, sleep recovery active agent, and optionally the next day active agent can be formulated as a single unit composition (for example a multilayered particle). For example, the single unit composition can be spherical bead, wherein the sleep recovery active agent and optional next day active agent can be located in the core of the bead, and the sleep quality active agent can be located as a first layer on the core's surface. Again, when the bead is ingested and digested, the timing of the release of the various active agents is in accordance with the timing of the bead's degradation in the gut or lower intestines. The sleep promoting active agent can then be administered as a separate composition along with the single unit composition containing the sleep quality active agent, the sleep recovery active agent, and the optional next day active agent. In some examples, the sleep promoting active agent along with the single unit composition can be dispersed in the comestible matrix and can be released by ingestion such as by chewing and/or swallowing or dissolution of the comestible matrix.

In some examples, the sleep promoting active agent, the sleep quality active agent, and optionally the next day active agent can be formulated as a single unit composition. In some examples, the sleep promoting active agent, optionally the sleep recovery active agent, and the next day active agent can be formulated as a single unit composition. The present disclosure is not limited by the particular combination of the sleep promoting active agent, sleep quality active agent, sleep recovery active agent, and/or the next day active agent.

In other examples, the sleep quality active agent, the sleep recovery active agent, and the next day active agent can each be formulated as separate beads (for example a single layered particle). For example, a spherical bead comprising the sleep quality active agent, a spherical bead comprising the sleep recovery active agent, and a spherical bead comprising the next day active agent can be administered together. The sleep quality active agent, sleep recovery active agent, or the next day active agent can be independently be located in the core or throughout the bead. One, two or all three of these beads can be coated with the sleep promoting active agent. Alternative, a separate sleep promoting bead can be used or the sleep promoting active agent can be part of a comestible matrix. An example of such a composition is disclosed in U.S. Pat. No. 8,545,892, which is incorporated by reference herein in its entirety for its teachings of beads for use in delivery of agents.

In some examples, the sleep promoting active agent, the sleep quality active agent, and the sleep recovery active agent, and optionally the next day active agent can be formulated as a single multilayered capsule. For example, the capsule can comprise a first layer comprising the sleep promoting active agent, a second layer (optionally disposed on the first layer) comprising the sleep quality active agent, a third layer (optionally disposed on the first or second layer) comprising the sleep recovery active agent, and optionally a fourth layer (optionally disposed on the second or third layer) comprising the next day active agent. When the bead is ingested and digested, the timing of the release of the various active agents is in accordance with the timing of the bead's degradation in the gut or lower intestines. Again, the active agent can be present in each layer for example, as a nanoparticle, a microparticle or a granule (including the active agent and a binder) or in its native form (that is, the active agent alone, not mixed with a binder). In some embodiments, the active agent (in the form of a nanoparticle, a microparticle, a granule, or its native form) can be combined with an additional material (such as a binder or bulking agent) to form a layer of the single unit or multi-unit composition.

The size of a single unit composition is not essential. The size of the single unit composition can be such that the composition can be seen in the comestible matrix without need for magnification, but also such that the composition is not substantially felt in the mouth or throat when being orally ingested. One suitable range for the diameter of the single unit composition is less than 5.0 mm, such as from 100 microns to 5.0 mm, from 300 microns to 5.0 mm, from 0.5 mm to 5.0 mm or from 0.5 mm to 2.5 mm The single unit composition can also be much smaller, such as on a micrometer or nanometer scale.

The compositions (for example each single unit composition), can further include a coating layer to further change the rate of release of the active agent. Additional coating layers will generally result in a delayed and/or slower release of the active agent. In some aspects, a thicker coating layer and/or crosslinked polymeric binders in the coating layer can result in a delayed and/or slower release of the active agent. In some aspects, the coating layer can be formulated such that external factors such as pH and osmosis can result in a delayed and/or sustained release of the active agent. In some examples, the coating layer can include a cellulose-based coating layer, such as an ethyl cellulose-based coating layer. The coating layer can be a SURELEASE™ coating layer as manufactured by Colorcon of West Point, Pa. The coating may be added in any amount to the compositions, for example, the coating can be added at less than about 15 wt % of the composition.

The compositions can also include additional components to alter the consistency, appearance, taste, smell, or shelf life of the beads or individual ingredients in the bead. These components may be added as either an additional ingredient in the beads, as a coating layer on an ingredient, or as a coating layer on the beads. In some examples, a coloring agent is used to alter the color of the beads. In some embodiments, a taste masking agent is used to alter the taste of the beads.

In some aspects, the composition can provide an immediate burst release of a sleep promoting active agent within about 30 minutes of administration. For example, the composition can provide an immediate burst release of the sleep promoting active agent from about 1 minute to about 30 minutes, about 1 minute to about 25 minutes, or about 1 minute to about 20 minutes after administration. In some examples, the composition can provide an immediate burst release of the sleep promoting active agent within about 30 minutes, about 25 minutes, about 20 minutes, about 15 minutes, about 10 minutes, about 9 minutes, about 8 minutes, about 7 minutes, about 6 minutes, about 5 minutes, about 4 minutes, about 3 minutes, about 2 minutes, or about 1 minute of administration. All or most (for example, 90% or greater) of the sleep promoting active agent may be released within this time. In some aspects, all or most of the sleep promoting active agent can be released within about 1 hour to about 3 hours. For example, all or most of the sleep promoting active agent may be released within about 1 hour, about 1.5 hour, about 2 hours, about 2.5 hours, or about 3 hours after administration.

In some aspects, the composition can also provide a burst release or sustained release of a sleep quality active agent within about 8 hours of administration. For example, the composition can provide a burst release or sustained release of the sleep quality active agent from about 10 minutes to about 8 hours, about 10 minutes to about 7 hours, about 10 minutes to about 6 hours, about 2 hours to about 6 hours, or about 2.5 hours to about 4.5 hours, after administration. In some embodiments, the composition can provide a burst release or sustained release of the sleep quality active agent within about 8 hours, about 7.5 hours, about 7 hours, about 6.5 hours, about 6 hours, about 5.5 hours, about 5 hours, or about 4.5 hours of administration. In some embodiments, the composition can provide a burst release or sustained release of the sleep quality active agent after about 1 hours, about 1.5 hours, about 2 hours, about 2.5 hours, about 3 hours, about 3.5 hours, about 4 hours, or about 4.5 hours of administration. Substantially all (for example, 90% or greater, 95% or greater, or 100%) of the sleep quality active agent may be released within this time.

In some aspects, the composition can further provide a delayed burst and/or delayed sustained release of a sleep recovery active agent after about 3 hours post administration. For example, the composition can provide a delayed burst or delayed sustained release of the sleep recovery active agent from about 3 hours to about 10 hours, about 3 hours to about 9 hours, about 3 hours to about 8 hours, about 4 hours to about 10 hours, about 4 hours to about 9 hours, about 4 hours to about 8 hours, about 5 hours to about 10 hours, about 6 hours to about 8.5 hours, or about 6.5 hours to about 8.5 hours, after administration. In some examples, the composition can provide a delayed burst or a delayed sustained release of the sleep recovery active agent after about 3 hours, about 3.5 hours, about 4 hours, about 4.5 hours, about 5 hours, about 5.5 hours, about 6 hours, or about 6.5 hours post administration. Substantially all (for example, 90% or greater, 95% or greater, or 100%) of the sleep recovery active agent may be released within this time.

In some aspects, the composition can further provide a sustained, delayed burst, or delayed sustained release of a next day active agent after about 3 hours post administration. For example, the composition can provide a delayed burst or delayed sustained release of the next day active agent from about 3 hours to about 10 hours, about 3 hours to about 9 hours, about 3 hours to about 8 hours, about 4 hours to about 10 hours, about 4 hours to about 9 hours, about 4 hours to about 8 hours, or about 5 hours to about 10 hours, after administration. In some examples, the composition can provide a delayed burst or a delayed sustained release of the next day active agent after about 3 hours, about 3.5 hours, about 4 hours, about 4.5 hours, about 5 hours, about 5.5 hours, about 6 hours, or about 6.5 hours post administration. Substantially all (for example, 90% or greater, 95% or greater, or 100%) of the next day active agent may be released within this time.

Methods of Making

The method of making the compositions disclosed herein is dependent on the desired rate of release of the active agent. The rate at which the active agent is released, for example under physiological conditions or in the stomach or the lower intestines can be controlled by the type and amount of binder used in the composition. A composition with relatively minor amounts of binding agents will be broken down quickly in the digestive tract, while compositions with higher amounts of binding agents and coatings will break down relatively slowly.

Methods of making a single unit composition comprising an active agent encapsulated in a binder is describe in U.S. Pat. No. 8,545,892, the disclosure of which is incorporated herein by reference. In short, the method can include blending the active agent, the binder, and a suitable solvent to form a mixture. The mixture can then be extruded and optionally unitized to form a single unit composition.

A multi-layered single unit composition can be prepared by first creating the core layer. The core layer can be prepared as described above. A first layer can be deposited on the outer surface of the core layer by mixing the core particle with a solution or suspension of the ingredients in the first layer. After deposition of the first layer on the core particle, the single unit dosage composition can be collected by centrifugation followed by washing. A second layer can be deposited on the outer surface of the first layer similar to deposition of the first layer.

The single unit composition can be dispersed in a comestible matrix by mixing the single unit dosage composition with any suitable comestible phase. For example, the single unit composition can be mixed with a chocolate base.

The composition comprising the single unit composition and the comestible matrix can be formulated as a daily oral single dosage form Methods of Using Methods of treating a sleep disorder or a subject having an abnormal sleep-wake cycle in a subject are also disclosed. Sleep disorder, as used herein includes, but is not limited to, insomnia, difficulty falling asleep, difficulty staying asleep, narcolepsy and its clinical manifestations such as sleep attacks, cataplexy, sleep paralysis, hypnagogic hallucinations, sleep apnea, hypersomnia, failure to wake-up feeling refreshed and rested or fatigue on waking, and related disorders. In some examples, the sleep disorder comprises fragmented sleep architecture.

In some aspects, treating a sleep disorder or modifying or improving the sleep-wake cycle in a subject includes improving sleep sensation determined by subjective judgment using psychological evaluation techniques or improving the sleep state determined objectively using techniques of estimating sleep and wakefulness states based on continuous recording of activity amounts. For example, the obstructive sleep apnea questionnaire can be used to examine the sleep sensation of the previous night to the present morning upon arising. The questionnaire is based on the five factors of sleepiness upon arising, sleep initiation and sleep maintenance, dream quality, recovery from fatigue, and elongation of sleep length and has been verified in regard to the reliability and validity of the respective factors.

Methods of sleep recovery including enhancing mental acuity or cognitive activity in a subject are also disclosed. Specifically, methods of sleep recovery after sleeping without unpleasant feeling or grogginess are disclosed. Sleep recovery can be determined objectively by measuring changes in the brain activity within the alpha frequency band using an electroencephalogram, or subjectively using the Toronto Hospital Alertness Test (THAT).

The method can include administering a sleep promoting active agent that provides a burst release of the sleep promoting active agent within about 30 minutes of administration, administering a sleep quality active agent in the form for a burst and/or sustained supply of the sleep quality active agent within about 6 hours of administration, administering a sleep recovery active agent after about 3 hours of administration of the sleep promoting active agent, and optionally administering a next day active agent in the form for a sustained, delayed burst, and/or delayed sustained supply of the next day active agent upon administration. The method can include administering one or more sleep promoting active agents that upon administration provides an immediate burst release of the sleep promoting active agents within about 30 minutes of administration, administering one or more sleep quality active agents that upon administration provides a delayed burst or delayed sustained release of the sleep quality active agents within about 6 hours of administration, and optionally administering a next day active agent that upon administration provides a sustained, delayed burst and/or delayed sustained release of the optional next day active agent. The method can include administering one or more sleep promoting active agents that upon administration provides an immediate burst release of the sleep promoting active agents within about 30 minutes of administration, optionally administering one or more sleep recovery active agents that upon administration provides a delayed burst or delayed sustained release of the sleep recovery active agents after about 3 hours of administration, and administering one or more next day active agent that upon administration provides a sustained, delayed burst, and/or delayed sustained release of the next day active agent. The method can include administering one or more sleep quality active agents that upon administration provides a delayed burst or delayed sustained release of the sleep quality active agents within about 6 hours of administration, and administering one or more sleep recovery active agents that upon administration provides a delayed burst or delayed sustained release of the sleep recovery active agents after about 3 hours of administration, and optionally administering one or more next day active agent that upon administration provides a delayed burst or delayed sustained release of the next day active agent after about 3 hours of administration. The method can include administering one or more sleep quality active agents that upon administration provides a delayed burst or delayed sustained release of the sleep quality active agents within about 6 hours of administration, and optionally administering one or more sleep recovery active agents that upon administration provides a delayed burst or delayed sustained release of the sleep recovery active agents after about 3 hours of administration, and administering one or more next day active agent that upon administration provides a delayed burst or delayed sustained release of the next day active agent after about 3 hours of administration. The method can include administering one or more sleep recovery active agents that upon administration provides a delayed burst or delayed sustained release of the sleep recovery active agents after about 3 hours of administration, and administering one or more next day active agent that upon administration provides a delayed burst or delayed sustained release of the next day active agent after about 3 hours of administration.

In some aspects, the methods of treating a subject with a sleep disorder or modifying or improving the sleep-wake cycle in a subject can include administering any one of the compositions described herein. In some aspects, the methods of treating a subject or modifying or improving the sleep-wake cycle in a subject with a sleep disorder can include administering two or more of the compositions described herein. The active agents can be administered simultaneously, for example in the form of a single unit composition or separately.

This composition is not limited in particular in terms of administration method, number of times of administration, administration period, etc., and can be administered once or in a plurality of times by a suitable form of administration. In some embodiments, the composition is administered orally, once daily.

In some examples, the sleep disorder is a dyssomnia. Dyssomnia can include psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change (jet lag) syndrome, shift work sleep disorder, irregular sleep-wake pattern, delayed sleep phase syndrome, advanced sleep phase syndrome and non-24-hour sleep-wake disorder.

In some examples, the sleep disorder is a parasomnia. Parasomnia can include confusional arousals, sleepwalking and sleep terrors, rhythmic movement disorder, sleep starts, sleep talking and nocturnal leg cramps.

In some examples, the sleep disorder is associated with a medical or psychiatric disorder. The medical or psychiatric disorder can include psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep disorder.

EXAMPLES

The following examples are set forth below to illustrate the compositions, methods, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Preparation of Soft Chew Composition

Capsules were prepared as detailed in Table 1 and as described below. Powders from each of the following active ingredient were prepared by mixing with a polymeric binder for 3 minutes in a low shear planetary mixer:
Valerian root extract
PHARMAGABA™
5-HTP (5-Hydroxytryptophan)
Melatonin, and
SUNTHEANINE™

Water was then added to the powder mixture to produce a wet mass. The wet mass was passed through an extruder at 50 rpm The extrudate was spheronized in a spheronizer at 1000 rpm for 1 minute to produce spherical beads. The spherical beads were dried until the moisture content was reduced to less than 5 wt %.

Compositions comprising RELORA™ and Valerian root extract were prepared as describe above, except a taste masking agent was used instead of a polymeric binder.

A sustained release capsule was prepared by mixing the beads prepared from the valerian root extract, PHARMAGABA™ 5-hydroxytryptophan, melatonin, SUNTHEANINE™, and RELORA™, as well as 5-hydroxytryptophan, magnesium glycinate, PHARMAGABA™ riboflavin 5'-phosphate sodium, pyridoxal-5-phosphate monohydrate, melatonin, (6S)-5-methyltetrahydrofolic acid, glucosamine salt, methylcobalamin with a comestible matrix.

A burst release capsule was prepared by mixing the taste masking beads prepared from the valerian root extract and RELORA™ as well as 5-hydroxytryptophan, magnesium glycinate, PHARMAGABA™, riboflavin 5'-phosphate sodium, pyridoxal-5-phosphate monohydrate, melatonin, (6S)-5-methyltetrahydrofolic acid, glucosamine salt, methylcobalamin with a comestible matrix.

The release time was determined based on dissolution times of each ingredient in water.

TABLE 2

| | Soft Chew Composition | | | | | |
|---|---|---|---|---|---|---|
| Ingredient Name | Burst Release (Powder in Soft Chew) | Burst Release (A) | Sustained Release (B) | Delayed and Sustained Release (C) | Total (m2s) | Release Time (Minutes) |
| 5-Hydroxytryptophan | 100.00 | | | | 100.00 | 0 |
| Magnesium Glycinate | 100.00 | | | | 100.00 | 0 |
| PHARMAGABA ™ | 100.00 | | | | 100.00 | 0 |
| Riboflavin 5'-Phosphate Sodium | 6.00 | | | | 6.00 | 0 |
| Vitamin B6 | 6.00 | | | | 6.00 | 0 |
| Melatonin | 3.30 | | | | 3.30 | 0 |
| QUATREFOLIC ™ | 1.20 | | | | 1.20 | 0 |
| Vitamin B12 | 0.24 | | | | 0.24 | 0 |
| RELORA ™ (taste masking bead) | | 250.00 | | | 250.00 | 5 |

TABLE 2-continued

| | Soft Chew Composition | | | | | |
|---|---|---|---|---|---|---|
| Ingredient Name | Burst Release (Powder in Soft Chew) | Burst Release (A) | Sustained Release (B) | Delayed and Sustained Release (C) | Total (m2s) | Release Time (Minutes) |
| Valerian Root Extract (taste masking bead) | 150.00 | | | | 150.00 | 5 |
| Valaerina Root Extract (polymeric bead) | | | 100.00 | | 100.00 | 90 |
| PHARMAGABA™ (polymeric bead) | | | 67.00 | | 67.00 | 90 |
| 5-Hydroxytryptophan (polymeric bead) | | | 50.00 | | 50.00 | 90 |
| Melatonin (polymeric bead) | | | 4.00 | | 4.00 | 90 |
| SUNTHEANINE™ (polymeric bead) | | | | 50.00 | 50.00 | 420 |

Figure 2A:
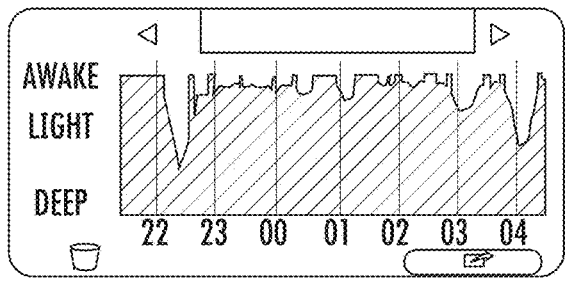
FIGS. 2A-2B are graphs showing the sleep pattern of a subject.
Figure 2B:
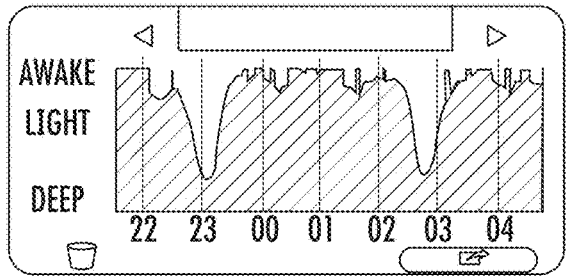

Sleep Profile:

The sleep profile of a subject was monitored using the app "Sleep Machine" by SleepSoft LLC on a smart phone (FIGS. 2A-2B). FIG. 2A is a control sleep profile in which the subject was not administered a sleep aid. FIG. 2B shows the sleep profile in the subject after administering the burst release capsule.

Example 2: Preparation of Soft Chew Composition

A capsule was prepared as detailed in Table 2 and as described below. Powders from each of the following active ingredient were prepared by mixing with a polymeric binder for 3 minutes in a low shear planetary mixer:
5-HTP (5-Hydroxytryptophan)
Melatonin, and
SUNTHEANINE™

Water was then added to the powder mixture to produce a wet mass. The wet mass was passed through an extruder at 50 rpm. The extrudate was spheronized in a spheronizer at 1000 rpm for 1 minute to produce nano beads. The nano beads were mixed with various excipients and water for 3 minutes in a low shear planetary mixer to produce a wet mass. The wet mass was passed through an extruder at 50 rpm. The extrudate was spheronized in a spheronizer at 1000 rpm for 1 minute to produce micro beads. The micro beads were dried until the moisture content was reduced to less than 5 wt %.

A capsule was prepared by mixing the micro beads with RELORA™, magnesium glycinate, PHARMAGABA™, 5-hydroxytryptophan, riboflavin 5'-phosphate sodium, pyridoxal-5-phosphate monohydrate, melatonin, QUATREFOLIC™, and methylcobalamin to produce a mixture. The mixture was placed in a vegetable capsule.

Figure 3:
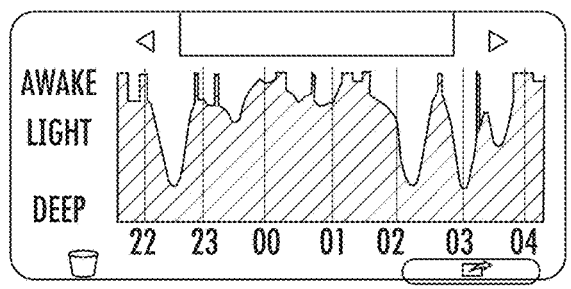
FIG. 3 is a graph showing the sleep pattern of a subject after administration of a vegetable capsule comprising sleep promoting active agents and sleep quality active agents.

The vegetable capsule was administered to a subject. The subject was monitored using the app "Sleep Machine" by SleepSoft LLC on an iphone (FIG. 3).

TABLE 3

| | Soft Chew Composition | | | | |
|---|---|---|---|---|---|
| Ingredient Name | Burst Release (Powder in Soft Chew) | Burst Release (A) | Sustained Release (B) | Delayed and Sustained Release (C) | Total (m2s) |
| 5-Hydroxytryptophan | 50.00 | | | | 50.00 |
| Magnesium Glycinate | 200.00 | | | | 200.00 |
| PHARMAGABA™ | 125.00 | | | | 125.00 |
| Riboflavin 5'-Phosphate Sodium | 6.00 | | | | 6.00 |
| Vitamin B6 | 6.00 | | | | 6.00 |
| Melatonin | 2.50 | | | | 2.50 |
| QUATREFOLIC™ | 1.20 | | | | 1.20 |
| Vitamin B12 | 0.24 | | | | 0.24 |
| RELORA™ | 250.00 | — | | | 250.00 |
| Total immediate release components | | | | | 641 |
| 5-Hydroxytryptophan (polymeric bead) | | | 50.00 | | 50.00 |
| Melatonin (polymeric bead) | | | 3.00 | | 3.00 |

TABLE 3-continued

| | Soft Chew Composition | | | | |
|---|---|---|---|---|---|
| Ingredient Name | Burst Release (Powder in Soft Chew) | Burst Release (A) | Sustained Release (B) | Delayed and Sustained Release (C) | Total (m2s) |
| SUNTHEANINE ™ (polymeric bead) | | | | 50.00 | 50.00 |
| Micro-bead excipients | | | | | 277.5 |
| Total microbead components | | | | | 381 |

Example 3: Exemplary Compositions

Tables 4 to 6 show exemplary sleep promoting, sleep quality, sleep recovery, and next day active ingredients, the amount and function of each ingredient.

TABLE 4

Exemplary sleep promoting and sleep quality active ingredients

| Ingredient | Amount (m2) | Mode of Action | Function |
|---|---|---|---|
| 5-Hydroxytryptophan, (extract from *Griffonia simplicifolia*) | 5-1,000 | serotonin & melatonin precursor | Sleep promoter |
| γ-aminobutyric acid (GABA) | 5-1,200 | inhibitory neurotransmitter | Sleep promoter |
| PharmaGaba | 5-800 | inhibitory neurotransmitter | sleep promoter |
| SunTheanine | 5-800 | brain wave modulator | anxiolytic |
| L-Theanine | 5-800 | brain wave modulator | anxiolytic |
| Glycine | 5-2,000 | NDMA receptor agonist | relaxant |
| Picamilon (nicotinoyl-GABA) | 5-2,000 | GABA derivative | sleep promoter |
| L-taurine | 5-1,200 | GABA receptor agonist | sleep promoter |
| Tryptophan (L-tryptophan) | 5-1,600 | serotonin & melatonin precursor | sleep promoter |
| Phosphatidylserine | 5-600 | cortisol blunting | anti-stress |
| L-glutamine | 5-3,000 | GABA precursor | anxiolytic |
| Pbenibut 4-Amino-3-Phenylbutyric Acid | 5-600 | GABA derivative | sleep promoter |
| Milk peptide | 5-300 | GABA receptor agonist | anxiolytic |
| Milk protein hydrolysate | 5-4,000 | GABA receptor agonist | anxiolytic |
| Lactium | 5-400 | GABA receptor agonist | anxiolytic |
| Eicosapentaenoic acid | 5-750 | anti-inflammatory | repair and recovery |
| RELORA | 5-1,000 | cortisol blunting | anti-stress |
| *Magnolia officinalis* (bark) | 5-2,000 | adenosine inhibitor, GABA agonist | anxiolytic |
| Extract from *Phellodendron amurense* (bark) | 5-2,000 | cortisol blunting | anti-stress |
| *Valeriana officinalis* extract (root) | 5-500 | GABA analog | sleep promoter |
| Hops, extract from *Humulus lupulus* | 5-1,600 | GABA promoter | anxiolytic |
| Passionflower (*Passiflora incarnate* extract) | 5-2,500 | GABA analog | sleep promoter |
| Lemon balm extract | 5-1,600 | GABA transaminase inhibitor | anxiolytic |
| Chamomile (*Matricaria chamomilla* extract) | 5-1,000 | | anxiolytic |
| Jujube extract | 5-600 | | anxiolytic |
| Catnip (*Nepeta cataria* extract) | 5-1,600 | | anxiolytic |
| Persian silk tree (*Albizia julibrissin* extract) | 5-1,600 | | |

TABLE 4-continued

Exemplary sleep promoting and sleep quality active ingredients

| Ingredient | Amount (m2) | Mode of Action | Function |
|---|---|---|---|
| *Melissa officinalis* L. leaf extract | 5-1,600 | GABA transaminase inhibitor | anxiolytic |
| Extract from *Hemerocallis Julva* var. *sempervirens* | 5-1,600 | | |
| St. John's wort extract | 5-1,600 | SSRI | anxiolytic |
| *Bacopa monnieri* extract | 5-1,600 | | anxiolytic |
| Luobuma (*Apocynum venetum* L. leaf extract) | 5-1,600 | | anxiolytic |
| Reishi mushroom (*Ganoderma lucidum* extract) | 5-2,000 | | anxiolytic |
| Kava | 5-600 | | anxiolytic |
| Ashwagandha extract | 5-1,100 | | anti stress |
| Skullcap (*Scutellaria baicalensis* extract) | 5-1,700 | | anxiolytic |
| Melatonin | 0.03-20 | hormone | regulates sleep wake cycle |
| Magnesium | 5-3,500 | electrolyte for muscle relaxation | relaxant/restless leg |
| Magnesium glycinate | 5-3,500 | electrolyte for muscle relaxation | relaxant/restless leg |
| Magnesium taurate | 5-900 | electrolyte for muscle relaxation | relaxant/restless leg |
| Magnesium chloride | 5-1,000 | electrolyte for muscle relaxation | relaxant/restless leg |
| Magnesium citrate | 5-1,500 | electrolyte for muscle relaxation | relaxant/restless leg |
| Magnesium oxide | 5-1,500 | electrolyte for muscle relaxation | relaxant/restless leg |
| Magnesium amino acid chelate | 5-500 | electrolyte for muscle relaxation | relaxant/restless leg |
| Calcium | 5-2,500 | electrolyte for muscle relaxation | relaxant/restless leg |
| Calcium D-glucarate | 5-2,500 | electrolyte for muscle relaxation | relaxant/restless leg |
| Calcium gluconate | 5-2,000 | electrolyte for muscle relaxation | relaxant/restless leg |
| Calcium lactate | 5-600 | electrolyte for muscle relaxation | relaxant/restless leg |
| Zinc | 1-100 | enzyme precursor | repair and recovery |
| Iron | 1-150 | | restless leg |
| Phosphatidyl serine | 5-700 | | |

TABLE 5

Exemplary sleep recovery active ingredients

| Ingredient | Amount (m2) |
|---|---|
| SunTheanine | 5-250 |
| L-Theanine | 5-300 |
| γ-aminobutyric acid (GABA) | 5-600 |
| Glycine | 5-1,000 |
| Folic acid | 0.033-0.85 |
| QUATREFOLIC ((6S)-5-methyltetrahydrafolic acid, glucosamine salt) | 0.033-0.4 |
| Inositol | 5-650 |
| Riboflavin 5'-phosphate sodium | 1-35 |
| Vitamin A | 100 IU-25,000 IUs |
| Vitamin B12 | 0.005-5 |
| Vitamin B12 (cyanocobalamin 1% trituration) | 0.005-5 |
| Vitamin B12 (methylcobalamm) | 0.005-5 |
| Vitamin B3 (niacin) | 5-750 |
| Vitamin B5 (7.8% calcium 87% pantothenate) | 5-1,200 |
| Vitamin B6 (pyridoxal 5 phosphate, P5P) | 1-300 |
| Vitamin B6 (pyridoxine HCL) | 1-600 |
| Vitamin B9 | 0.005-2 |
| Vitamin C | 5-3,000 |
| Vitamin D3 (cholecalciferol) | 5-7,500 |
| Camosin | 5-1,200 |
| Caffeine | 5-900 |
| Xanthines (theobromine and caffeine) | 1-900 |
| Cocoa Extract (Chocamine) | 1-600 |
| Ephedra | 1-750 |
| *Bacopa monnieri* extract | 5-900 |
| Vincamine | 1-100 |
| *GinkRo biloba* extract | 5-500 |
| *Eleutherococcus senticosus* extract | 5-500 |
| *Centella asiatica* extract | 5-500 |
| Panax ginseng | 5-1,500 |
| Peppermint extract | 5-1,500 |
| Rosemary extract | 5-1,500 |
| Wild oats extract | 5-900 |
| L-taurine | 5-1,500 |
| Alpha-glycerylphosphoryl choline | 5-900 |
| lecithin | 5-2,500 |

TABLE 5-continued

Exemplary sleep recovery active ingredients

| Ingredient | Amount (m2) |
|---|---|
| cytidine diphosphate-choline | 5-800 |
| Phosphatidyl serine | 5-900 |
| ATP | 5-300 |
| *Coleus forshkolii* extract | 5-750 |
| Glycine | 5-2,000 |
| Ribose | 5-3,000 |
| Magnesium | 5-3,000 |
| Coenzyme Q10 | 5-800 |

TABLE 6

Exemplary next day active ingredients

| Ingredient | Amount (m2) |
|---|---|
| Folic acid | 0.033-0.85 |
| QUATREFOLIC ((6S)-5-methyltetrahydrofolic acid, glucosamine salt) | 0.033-0.4 |
| Inositol | 5-650 |
| Riboflavin 5'-phosphate sodium | 1-35 |
| Vitamin A | 100 IU-25,000 IUs |
| Vitamin B12 | 0.005-5 |
| Vitamin B12 (cyanocobalamin 1% trituration) | 0.005-5 |
| Vitamin B12 (methylcobalamin) | 0.005-5 |
| Vitamin B3 (niacin) | 5-750 |
| Vitamin B5 (7.8% calcium 87% pantothenate) | 5-1,200 |
| Vitamin B6 (pyridoxal 5 phosphate, P5P) | 1-300 |
| Vitamin B6 (pyridoxine HCL) | 1-600 |
| Vitamin B9 | 0.005-2 |
| Vitamin C | 5-3,000 |
| Vitamin D3 (cholecalciferol) | 5-7,500 |
| Alpha-glycerylphosphoryl choline | 5-900 |
| lecithin | 5-2,500 |
| cytidine diphosphate-choline | 5-800 |
| Phosphatidyl serine | 5-900 |
| ATP | 5-300 |
| *Coleus forshkolii* extract | 5-750 |
| Glycine | 5-2,000 |
| Ribose | 5-3,000 |
| Magnesium | 5-3,000 |
| Coenzyme Q10 | 5-800 |

Example 4: Exemplary Composition

Table 7 shows an exemplary formulation comprising sleep promoting, sleep quality, and sleep recovery active ingredients.

TABLE 7

Sleep Formulation.

| Sleep Promoting (Sleep Onset Latency) Active Agents for Immediate Release | |
|---|---|
| Melatonin/mg | 0.1-0.5 |
| Lactium (milk peptides)/mg | 100-110 |
| L-tryptophan/mg | 190-210 |
| GABA (gamma-aminobutyric acid)/mg | 90-110 |
| Magnesium (from magnesium oxide)/mg | 240-260 |

TABLE 7-continued

Sleep Formulation.

| Sleep Quality (Sleep Maintenance) Active Agents for Release from about 2.5 to 4.5 hours | |
|---|---|
| Valerian root extract/mg | 140-160 |
| Relora (*Magnolia officinalis* and *Phellodendron amurense* extracts) I mg | 140-160 |
| Lemon Balm (*Melissa officinalis*) extract/mg | 30-50 |
| Hops extract (*Humulus lupus*)/mg | 20-40 |
| Sleep Recovery and/or Next Day (Morning Recovery) Active Agents for Release 6.5 to 8.5 hours | |
| Cocoa Extract I mg | 180-340 |
| L-Theanine/mg | 40-60 |
| Vitamin B5 (7.8% calcium 87% pantothenate)/mg | 30-50 |
| Vitamin B6 (pyridoxine HCL, USP)/mg | 1-3 |
| Vitamin B12 (cyanocobalamin 1% trituration)/mg | 0.2-0.5 |
| Folic Acid (97 to 102 using USB)/mg | 0.3-0.5 |

The exemplary formulation provided in Table 7 can be formulated into a multilayer capsule. The capsule can include a layer comprising two or more of the sleep promoting active agents and optionally a binder, a layer comprising two or more of the sleep quality active agents and a polymeric binder, and a layer comprising two or more of the sleep recovery active agents and a polymeric binder. The capsule can be administered with a beverage such as water, juice, or a drink.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition comprising:
   a bead comprising one or more sleep promoting active agents, and
   a bead comprising one or more sleep quality active agents, wherein upon administration to a subject there is:
   an immediate burst release of the one or more sleep promoting active agents within about 30 minutes of administration, and
   delayed release of the one or more sleep quality active agents from about 1 hour to about 6 hours after administration of the composition, and
   wherein each active agent is independently a phytochemical, a herbal extract, a vitamin, a hormone, an amino acid, a mineral, or combinations thereof.

2. The composition of claim 1, wherein delayed release of the sleep quality active agents is selected from a delayed burst release, a delayed sustained release, and combinations thereof.

3. The composition of claim 1, wherein the composition comprises at least two sleep promoting active agents selected from the group consisting of melatonin, L-theanine, γ-aminobutyric acid (GABA), casein decapeptide, L-tryptophan, and magnesium.

4. The composition of claim 1, wherein the composition comprises at least two sleep quality active agents selected from the group consisting of Valerian root extract, hops extract, lemon balm extract, melatonin, and an extract from *Magnolia*.

5. The composition of claim 1, wherein the composition comprises at least two sleep quality active agents selected from the group consisting of Valerian root extract, hops extract, lemon balm extract, and melatonin.

6. The composition of claim 1, wherein delayed sustained release of at least a portion of the sleep quality active agents is within 2 to 5 hours of administration.

7. The composition of claim 1, wherein the sleep quality active agent has a sustained release of 2.5-4.5 hours.

8. The composition of claim 1, wherein delayed release of the sleep quality active agents comprises a delayed sustained release of the sleep quality active agents.

9. The composition of claim 1, wherein the composition further comprises one or more sleep recovery active agent and/or one or more next day active agents having delayed release after about 6 hours from administration of the composition.

10. The composition of claim 9, wherein the one or more sleep recovery active agents when present, are selected from the group consisting of L-theanine, L-taurine, γ-aminobutyric acid, glycine, folic acid, (6S)-5-methyltetrahydrofolic acid or a salt thereof, inositol, riboflavin 5'-phosphate or a salt thereof, vitamin A, vitamin B12, methylcobalamin, cyanocobalamin, vitamin B3, vitamin B5, vitamin B6, pyridoxine, vitamin B9, vitamin C, vitamin D3, a xanthine, carnosine, alpha-glycerylphosphoryl choline, lecithin, cytidine diphosphate choline, phosphatidyl serine, ATP, ribose, magnesium, coenzyme Q10, extract from *Coleus forskohlii*, extract from *Bacopa monnieri*, caffeine, ephedra, vincamine, cocoa extract, extract from *Ginkgo biloba, Panax ginseng*, extract from *Eleutherococcus senticosus*, extract from *Centella asiatica*, peppermint extract, rosemary extract, wild oats extract, blends thereof, and combinations thereof.

* * * * *